United States Patent [19]
Casciani et al.

[11] Patent Number: 5,421,329
[45] Date of Patent: Jun. 6, 1995

[54] PULSE OXIMETER SENSOR OPTIMIZED FOR LOW SATURATION

[75] Inventors: James R. Casciani, Cupertino; Paul D. Mannheimer, Belmont; Steve L. Nierlich, Oakland; Stephen J. Ruskewicz, Kensington, all of Calif.

[73] Assignee: Nellcor, Inc., Pleasanton, Calif.

[21] Appl. No.: 221,911

[22] Filed: Apr. 1, 1994

[51] Int. Cl.$^6$ .............................................. A61B 5/00
[52] U.S. Cl. .................................... 128/633; 128/664; 128/666; 356/41
[58] Field of Search .............................. 128/633–634, 128/664–666; 356/41

[56] References Cited

U.S. PATENT DOCUMENTS

| | | |
|---|---|---|
| 3,638,640 | 2/1972 | Shaw . |
| 3,847,483 | 11/1974 | Shaw et al. . |
| 4,223,680 | 9/1980 | Jöbsis . |
| 4,623,248 | 11/1986 | Sperinde . |
| 4,714,341 | 12/1987 | Hamaguri et al. . |
| 4,859,057 | 8/1989 | Taylor et al. . |
| 5,109,849 | 5/1992 | Goodman et al. ................... 128/670 |
| 5,188,108 | 2/1993 | Secker . |
| 5,247,932 | 9/1993 | Chung et al. ......................... 128/633 |
| 5,299,570 | 4/1994 | Hatshek ............................... 128/633 |

OTHER PUBLICATIONS

*Effect Of Anemia On Pulse Oximeter Accurancy At Low Saturation*, J. W. Severinghaus, & S. O. Koh, Journal of Clinical Monitoring, vol. 6, No. 2, Apr. 1990, pp. 85–88.
*Design & Evaluation of a New Reflectance Pulse Oximeter Sensor*, Y. Mendelson et al., Medical Instrumentation, vol. 22, No. 4, Aug. 1988, pp. 167–173.
*Errors in 14 Pulse Oximeters During Profound Hypoxia*, J. W. Severinghaus et al., Journal of Clinical Monitoring, vol. 5, No. 2, Apr. 1989, pp. 72–81.
*Accuracy of Response of Six Pulse Oximeters to Profound Hypoxia*, J. W. Severinghaus et al., Anesthesiology, vol. 67, No. 4, Oct. 1987, pp. 551–558.
*The influence of changes in blood flow on the accuracy of pulse oximetry in humans*, M. Vegfors et al., Acta Anaesthesial Scand 1992: 36: 346–349.
*Evaluation of Light-Emitting Diodes for Whole Blood Oximetry*, A. P. Shepherd et al., IEEE Transactions on Biomedical Engineering, vol. BME-31, No. 11, Nov. 1984, pp. 723–725.
*Noninvasive Methods for Estimating In Vivo Oxygenation*, D. A. Benaron et al., Clinical Pediatrics, May 1992, pp. 258–273.
*In Vivo Reflectance of Blood and Tissue as a Function of Light Wavelength*, W. Cui et al., IEEE Transactions on Biomedical Engineering, vol. 37, No. 6, Jun. 1990, pp. 632–639.
Various excerpts from chapter entitled, Equipment, Monitoring, and Engineering Technology IV, Anesthesiology, vol. 71, No. 3A, Sep. 1989, A366–A373.
*Experimental and Clinical Evaluation of a Noninvasive Reflectance Pulse Oximeter Sensor*, S. Takatani et al., Journal of Clinical Monitoring, vol. 8, No. 4, Oct. 1992, pp. 257–266.
*Noninvasive measurement of regional cerebrovascular oxygen saturation in humans using optical spectroscopy*, P. W. McCormick et al., Time-Resolved Spectroscopy and Imaging of Tissues (1991), SPIE vol. 1431, pp. 294–302.
*Statistics of penetration depth of photons re-emitted from irradiated tissue*, G. H. Weiss et al., Journal of Modern Optics, 1989, vol. 36, No. 3, pp. 349–359.

Primary Examiner—William E. Kamm
Assistant Examiner—Robert L. Nasser, Jr.
Attorney, Agent, or Firm—Townsend and Townsend Khourie and Crew

[57] ABSTRACT

A pulse oximeter sensor with a light source optimized for low oxygen saturation ranges and for maximizing the immunity to perturbation induced artifact. Preferably, a red and an infrared light source are used, with the red light source having a mean wavelength between 700–790 nm. The infrared light source can have a mean wavelength as in prior art devices used on adults. The sensor of the present invention is further optimized by arranging the spacing between the light emitter and light detectors to minimize the sensitivity to perturbation induced artifact. The present invention optimizes the chosen wavelengths to achieve a closer matching of the absorption and scattering coefficient products for the red and IR light sources. This optimization gives robust readings in the presence of perturbation artifacts including force variations, tissue variations and variations in the oxygen saturation itself.

14 Claims, 12 Drawing Sheets

| EXTINCTION-SCATTERING COEFFICIENT PRODUCT (L/mmole-cm²) | 660 nm | 732 nm | 892 nm |
|---|---|---|---|
| μ's · β$_{HbO2}$ | 1.23 | 1.31 | 2.82 |
| μ's · β$_{85\%}$ | 2.67 | 1.63 | 2.64 |
| μ's · β$_{40\%}$ | 7.00 | 2.58 | 1.84 |
| μ's · β$_{Hb}$ | 10.85 | 3.41 | 1.59 |

735 nm

PULSE OXIMETER SENSOR OPTIMIZED FOR LOW SATURATION

BACKGROUND OF THE INVENTION

Pulse oximetry is used to continuously monitor the arterial blood oxygen saturation of adults, pediatrics and neonates in the operating room, recovery room, intensive care units, and increasingly on the general floor. A need exists for pulse oximetry in the delivery room for monitoring the oxygen status of a fetus during labor and delivery, and for monitoring the oxygen status of cardiac patients.

Pulse oximetry has traditionally been used on patient populations where arterial blood oxygen saturation is typically greater than 90%, i.e., more than 90% of the functional hemoglobin in the arterial blood is oxyhemoglobin and less than 10% is reduced hemoglobin. Oxygen saturation in this patient population rarely drops below 70%. When it does drop to such a low value, an unhealthy clinical condition is indicated, and intervention is generally called for. In this situation, a high degree of accuracy in the estimate of saturation is not clinically relevant, as much as is the trend over time.

Conventional two wavelength pulse oximeters emit light from two Light Emitting Diodes (LEDs) into a pulsatile tissue bed and collect the transmitted light with a photodiode positioned on an opposite surface (transmission pulse oximetry), or an adjacent surface (reflectance pulse oximetry). The LEDs and photodetector are housed in a reusable or disposable sensor which connects to the pulse oximeter electronics and display unit. The "pulse" in pulse oximetry comes from the time varying amount of arterial blood in the tissue during the cardiac cycle, and the processed signals from the photodetector create the familiar plethysmographic waveform due to the cycling light attenuation. For estimating oxygen saturation, at least one of the two LEDs' primary wavelength must be chosen at some point in the electromagnetic spectrum where the absorption of oxyhemoglobin ($HbO_2$) differs from the absorption of reduced hemoglobin (Hb). The second of the two LEDs' wavelength must be at a different point in the spectrum where, additionally, the absorption differences between Hb and $HbO_2$ are different from those at the first wavelength. Commercial pulse oximeters utilize one wavelength in the red part of the visible spectrum near 660 nanometers (nm), and one in the near infrared part of the spectrum in the range of 880 nm–940 nm (See FIG. 1). Photocurrents generated within the photodetector are detected and processed for measuring the modulation ratio of the red to infrared signals. This modulation ratio has been observed to correlate well to arterial oxygen saturation as shown in FIG. 2. Pulse oximeters and pulse oximetry sensors are empirically calibrated by measuring the modulation ratio over a range of in vivo measured arterial oxygen saturations ($SaO_2$) on a set of patients, healthy volunteers, or animals. The observed correlation is used in an inverse manner to estimate saturation ($SpO_2$) based on the real-time measured value of modulation ratios. (As used herein, $SaO_2$ refers to the in vivo measured functional saturation, while $SpO_2$ is the estimated functional saturation using pulse oximetry.)

The choice of emitter wavelengths used in conventional pulse oximeters is based on several factors including, but not limited to, optimum signal transmission through blood perfused tissues, sensitivity to changes in arterial blood oxygen saturation, and the intensity and availability of commercial LEDs at the desired wavelengths. Traditionally, one of the two wavelengths is chosen from a region of the absorption spectra (FIG. 1) where the extinction coefficient of $HbO_2$ is markedly different from Hb. The region near 660 nm is where the ratio of light absorption due to reduced hemoglobin to that of oxygenated hemoglobin is greatest. High intensity LEDs in the 660 nm region are also readily available. The IR wavelength is typically chosen near 805 nm (the isosbestic point) for numerical convenience, or in the 880–940 nm band where additional sensitivity can be obtained because of the inverse absorption relationship of Hb and $HbO_2$. Unfortunately, pulse oximeters which use LED wavelengths paired from the 660 nm band and 900 nm bands all show diminished accuracy at low oxygen saturations.

SUMMARY OF THE INVENTION

According to the invention, more accurate estimates of low arterial oxygen saturation using pulse oximetry are achieved by optimizing a wavelength spectrum of first and second light sources so that the saturation estimates at low saturation values are improved while the saturation estimates at high saturation values are minimally adversely affected as compared to using conventional first and second wavelength spectrums. It has been discovered that calculations at low saturation can be significantly improved if the anticipated or predicted rates of absorption and scattering of the first wavelength spectrum is brought closer to, optimally equal to, the anticipated or predicted rates of absorption and scattering of the second wavelength spectrum than otherwise exists when conventional wavelength spectrum pairs are chosen, such as when conventionally using a first wavelength centered near 660 nm and a second wavelength centered anywhere in the range of 880 nm–940 nm.

The present invention solves a long felt need for a pulse oximeter sensor and system which provides more accurate estimates of arterial oxygen saturation at low oxygen saturations, i.e. saturations equal to or less than 80%, 75%, 70%, 65%, or 60%, than has heretofore existed in the prior art. The sensor and system is particularly useful for estimating arterial saturation of a living fetus during labor where the saturation range of principal importance and interest is generally between 15% and 65%, and is particularly useful for estimating arterial saturation of living cardiac patients who experience significant shunting of venous blood into their arteries in their hearts and hence whose saturation range of principle importance and interest is roughly between 50% and 80%. By contrast, a typical healthy human has a saturation greater than 90%. The invention has utility whenever the saturation range of interest of a living subject, either human or animal, is low.

In addition to providing better estimates of arterial oxygen saturation at low saturations, the sensor and system of the invention further provide better and more accurate oxygen saturation estimates when perturbation induced artifacts exist and are associated with the subject being monitored.

When the rates of absorption and scattering by the tissue being probed by the first and second wavelength spectrums are brought closer together for the saturation values of particular interest, improved correspondence and matching of the tissue actually being probed by the first and second wavelengths is achieved, thus drastically reducing errors introduced due to perturbation induced artifacts. For example, when light of one wavelength is absorbed at a rate significantly higher than that of the other wavelength, the light of the other wavelength penetrates significantly further into the tissue. When the tissue being probed is particularly in-homogenous, this difference in penetrations can have a significant adverse impact on the accuracy of the arterial oxygen saturation estimate.

Perturbation induced artifacts include, but are not limited to, any artifact that has a measurable impact on the relative optical properties of the medium being probed. Perturbation induced artifacts include but are not limited to the following:

(1) variations in the tissue composition being probed by the sensor from subject to subject, i.e., variations in the relative amounts of fat, bone, brain, skin, muscle, arteries, veins, etc.;

(2) variations in the hemoglobin concentration in the tissue being probed, for example caused by vasal dilations or vasal constrictions, and any other physical cause which affects blood perfusion in the tissue being probed; and (3) variations in the amount of force applied between the sensor and the tissue being probed, thus affecting the amount of blood present in the nearby tissue.

In one embodiment, the present invention provides a fetal pulse oximeter sensor with a light source optimized for the fetal oxygen saturation range and for maximizing the immunity to perturbation induced artifact. Preferably, a "red" and an "infrared" light source are used, with the "red" light source having a mean wavelength between 700-790 nm. The "infrared" light source can have a mean wavelength as in prior art devices used on adults, i.e., between 800-1000 nm.

The fetal sensor of the present invention is further optimized by arranging the spacing between the light emitter and light detectors to minimize the sensitivity to perturbation induced artifact. The present invention recognizes that the typical oxygen saturation value for a fetus is in the range of 5-65%, commonly 15-65%, compared to the 90% and above for a typical adult. In addition, a fetal sensor is subject to increased perturbation induced artifact. Another unique factor in fetal oximetry is that the sensor is typically inserted through the uterus and the precise location where it lands is not known in advance.

The present invention recognizes all of these features unique to fetal oximetry and provides a sensor which optimizes the immunity to perturbation induced artifacts. This optimization is done with a trade-off on the sensitivity to changes in saturation value. This trade-off results in a more reliable calculation that is not obvious to those who practice the prior art methods which attempt to maximize the sensitivity to changes in the saturation value.

DETAILED DESCRIPTION OF THE PREFERRED EMBODIMENTS

Figure 3:
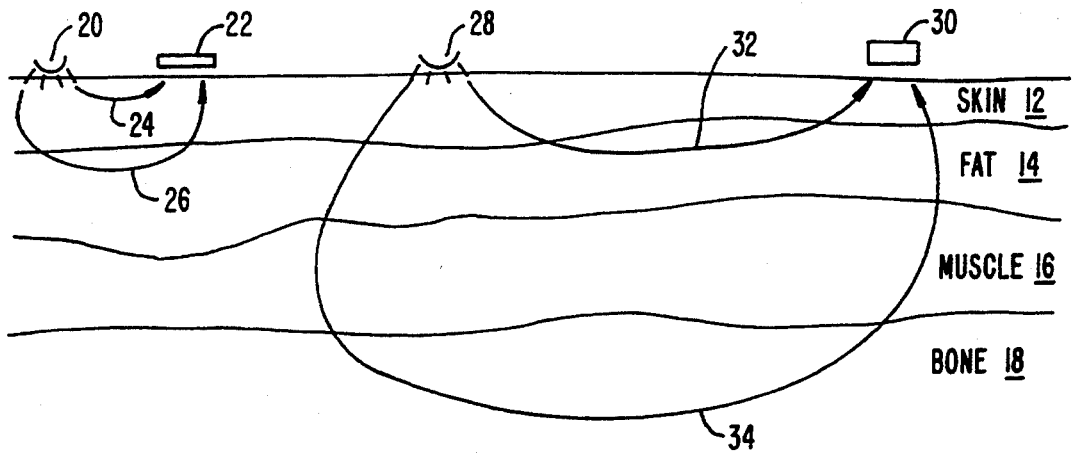
FIG. 3 is a diagram illustrating light penetration through different layers of tissue at different distances.

An understanding of the design of the fetal sensor according to the present invention requires an understanding of the environment in which the sensor will operate. FIG. 3 illustrates the layers of tissue in a typical fetus location where a sensor may be applied. Typically, there would be a first layer of skin 12, perhaps followed by a layer of fat 14, a layer of muscle 16, and a layer of bone 18. This is a simplified view for illustration purposes only. The contours and layers can vary at different locations. For instance, bone would be closer to the surface on the forehead, as opposed to closer muscle on the neck. Such variations in sites can produce the first type of perturbation artifact mentioned in the summary—artifact due to variations in tissue composition.

The general paths of light from an emitter 20 to a photodetector 22 are illustrated by arrows 24 and 26. Arrow 24 shows light which passes almost directly from emitter 20 to detector 22, basically shunted from one to the other, passing through very little blood perfused tissue. Arrow 26, on the other hand, illustrates the deeper penetration of another path of the light. The depth of penetration is affected by the wavelength of the light at low saturation. Longer wavelength light will penetrate deeper, with infrared penetrating deeper than red light, for instance. The deeper penetration can result in an undesirable variation between the infrared and red signals, since the IR signal will pass through more different layers.

Also illustrated in FIG. 3 is the effect of using an emitter 28 which is spaced at a greater distance from a detector 30 than the first pair 20, 22 described. As can be seen, this greater separation results in the penetration of a larger amount of tissue, as indicated by arrows 32 and 34. Thus, the greater spacing increases the depth of penetration, although it will reduce the intensity of the signal received at the detector due to more attenuation from more of the light being absorbed in the tissue and the greater light propagation distances involved.

The second type of perturbation mentioned in the summary is variations in the concentration of blood in the tissue from patient to patient or over time. A lower concentration results in less absorption, increasing the penetration depth. The inventors estimate that the mean penetration depth of photons in a medium is related to the product of the absorption and scattering coefficients, and this estimate is consistent with the findings of Weiss et al., *Statistics of Penetration Depth of Photons*

*Re-emitted from Irradiated Tissue,* Journal of Modern Optics, 1989, vol. 26, No. 3, 349-359, 354.

Figures 4A, 4B:
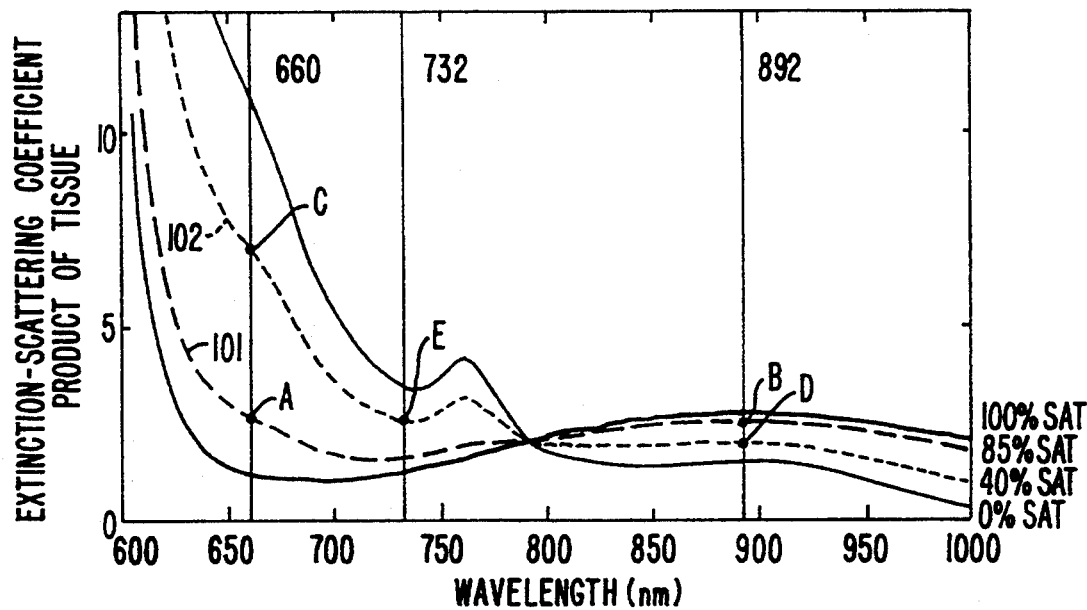
FIG. 4A is a chart of the variation in extinction and scattering coefficients over a range of wavelengths for different saturation values.
FIG. 4B is a table of the values of FIG. 4A.

FIG. 4A is a graph showing the product of the absorption and scattering coefficients for 0%, 40%, 85% and 100% saturations for wavelengths between 600 nm and 1,000 nm. For 85-100% tissue oxygen saturation, good balance or correlation exists between the product of the absorption and scattering coefficients of conventionally chosen wavelength pairs (i.e., 660 nm and 892 nm), as illustrated by points A and B on curve 101.

For low tissue oxygen saturation, points C and D on curve 102 graphically indicate than there is a very significant mismatch between the product of the absorption and scattering coefficients of the 660 nm red and 892 nm infrared light, with the red light being more strongly absorbed and scattered. This very significant absorption and scattering mismatch results in very different tissue being probed by the red and infrared light which significantly degrades the accuracy of the arterial oxygen saturation calculation. In addition, when a large range of low arterial oxygen saturations need to be accurately calculated, as when monitoring a fetus during labor where the range of arterial oxygen saturations can extend between 15% and 65%, it is evident from FIG. 4A that not only does a significant mismatch between the rates of absorption and scattering of the red and infrared light exist, but that the amount of mismatch will vary significantly as arterial oxygen saturation varies, thus causing a differential inaccuracy of oxygen saturation estimates which varies with the arterial saturation.

On the other hand, points D and E on curve 102 in FIG. 4A illustrate advantages of a preferred embodiment of the invention of choosing first and second wavelengths, i.e., 732 nm and 892 nm, which have absorption and scattering characteristics which are more closely balanced as compared to the prior art pairing of 660 nm and 892 nm for 40% tissue oxygen saturation. As can be appreciated, since the 732 nm extinction and scattering coefficients more nearly match the 892 nm extinction and scattering coefficients, improved overlap of the tissue being probed by the two wavelengths of light result. In addition, 732 nm results in a smaller variation of the extinction and scattering coefficients as a function of oxygen saturation as compared to 660 nm, thus resulting in better and more accurate oxygen saturation estimates over a wider range of saturations.

Wavelengths are preferably chosen whose product of their extinction and scattering coefficients form first and second values, a ratio between said first and second values being between 0.5 and 2 for a majority of the oxygen saturation reading range of zero to 65%. The tissue oxygen saturation values shown in FIG. 4A are closely correlated to arterial oxygen saturation values. In general, a given value of tissue oxygen saturation corresponds to a higher value of arterial oxygen saturation. For example, the inventors estimate that 85% tissue oxygen saturation corresponds to roughly 100% arterial oxygen saturation.

A preferred embodiment of the invention is to optimize the wavelengths used for a sensor to estimate fetal arterial oxygen saturation during labor where the saturation of interest is below 70%, a typical range of interest being between 15% and 65%. Attempting to match or balance the rates of absorption and scattering of the two wavelengths in a fetal sensor is particularly useful since the amount of perturbation induced artifacts are so severe in number and magnitude. For example, for a surface reflection sensor, it is difficult to know a priori where on the fetus the sensor will be located. For example, sometimes it will be on the head, other times the cheek. Hence, the tissue composition varies from application to application. In addition, the force by which the sensor is applied will vary during labor thus introducing still additional perturbation induced artifacts.

Another preferred embodiment of the invention is to use the sensor of the invention for cardiac patients whose range of saturation, where accuracy in calculations is important, is from 50% to 80%.

Figure 5:
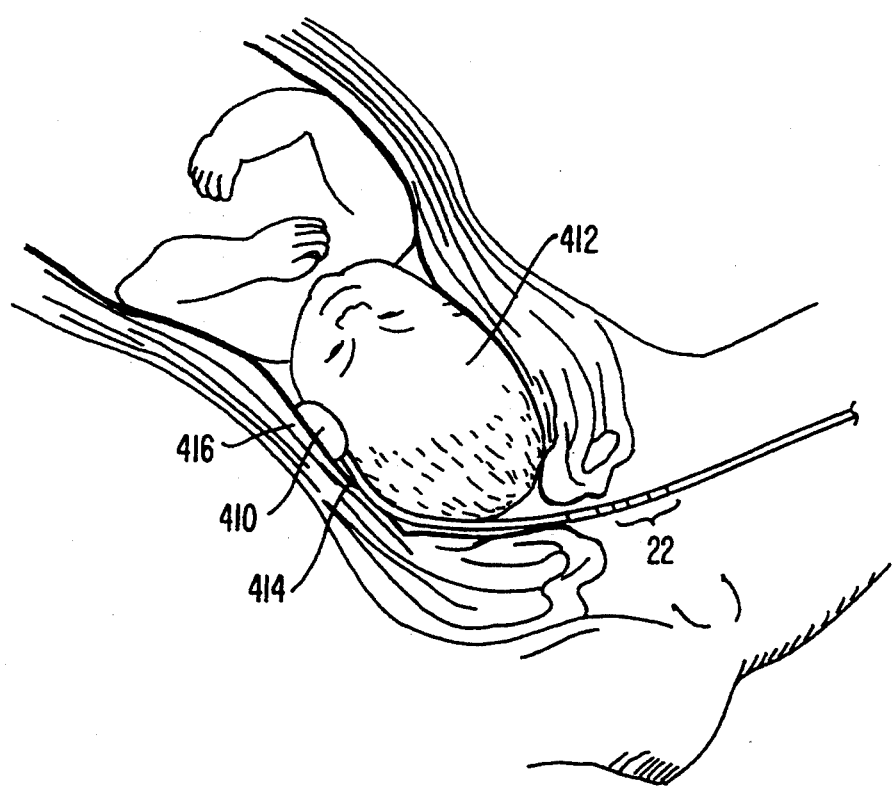
FIG. 5 is a diagram illustrating the placing of a sensor on a fetus.

FIG. 5 illustrates the placement of a sensor 410 on a fetus 412. The sensor is connected by a cable 414 to an external pulse oximeter monitor. As can be seen, sensor 410 is wedged between a uterine wall 416 and the fetus 412. In this instance, the sensor is on the side of the fetus' forehead. This wedging of the sensor applies a force to the skin immediately below the sensor, which reduces the amount of blood, causing exsanguination of the tissue. This reduces the amount of blood the light signal will pass through, thus increasing the difficulty of obtaining an accurate blood oxygenation reading.

Figure 6:
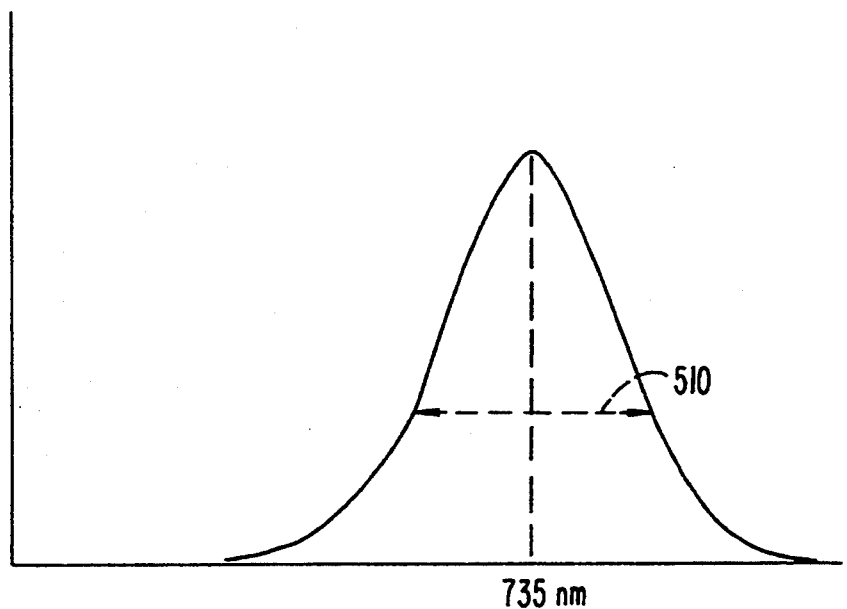
FIG. 6 is a graph illustrating the spectrum of an LED according to the present invention.

In choosing an optimum LED wavelength, it must be kept in mind that LEDs have a spectral width, and are not a single narrowband wavelength device like a laser. FIG. 6 illustrates the spectral spread of one preferred wavelength for a sensor according to the present invention, showing the red wavelength at 735 nm as being the peak wavelength. However, arrow 510 indicates a distribution of wavelengths which can be approximately 25 nm wide at which the intensity level is approximately 50% of that of the peak wavelength. In addition, when manufacturing LEDs, it is difficult to tightly control the mean wavelength. Thus, a purchaser specifying a particular wavelength, such as a 735 nm wavelength in an embodiment of the present invention, will expect to receive LEDs whose actual mean wavelength can vary by 10, 20 or more nanometers from the specified value. A narrow range is typically achieved by testing and sorting, which adds to the cost of the LEDs.

Preferably, with such a variation in mean wavelength, the red light source is chosen so that even if 735nanometers is not the mean, 735 nanometers will have an intensity of at least 50% of the intensity of the peak or any other wavelength in the spectrum.

The inventors of the present invention use both modeling and prototypes to achieve the optimized sensor set forth herein. Several theoretical models exist for describing the scattering of light within tissue. The models used by the inventors assume isotropic scattering within a homogeneous tissue bed. Even though this is a simplification of the true nature of light scattering in tissue (tissue is inhomogeneous and light is scattered primarily in the forward direction), these models are useful for predicting behaviors of pulse oximetry, and the sensitivity to many design parameters.

Utilizing such a model, different choices of LED wavelengths were explored. Tissue characteristics were numerically defined and the basis (calibration) correlation between $SaO_2$ and modulation ratio was calculated for each wavelength pair considered. Change in physiological condition was simulated by revising one or more of the numerically defined physical parameters. $SpO_2$ was recalculated from the resulting modulation ratio, and the saturation region where errors were minimized was noted. For saturations above 80% the conventional wavelength choice of 660 nm paired with 890 nm results in optimum performance, while for saturations below 70%, 735 nm band emitters paired with 890 nm gives improved stability.

FIGS. 7 through 18 show the predicted errors due to changing the tissue blood volume to one fourth the basis value for a variety of red and IR LED wavelength pairs. The A figures (such as 7A) show the modulation ratio vs. $SaO_2$. The B figures (7B) show the saturation error vs. $SaO_2$. This perturbation simulates the effects of blood volume variations within the patient population, anemia, ischemia, or localized exsanguination of blood in the tissue.

Sensitivity of the calibration to a change in tissue blood concentration is shown for several pairings of "red" and "IR" wavelengths. In each case, the LED has no secondary emission, and the perturbation is in going from a nominal 2% blood concentration in the tissue to 0.5%.

| | Figure Table | | |
|---|---|---|---|
| | | "IR" LED | |
| "red" LED | 805 nm | 890 nm | 940 nm |
| 660 nm | 7 | 8 | 9 |
| 700 nm | | 10 | |
| 730 nm | 11 | 12 | 13 |
| 760 nm | 14 | 15 | 16 |
| 790 nm | | 17 | 18 |

Figure 7A:
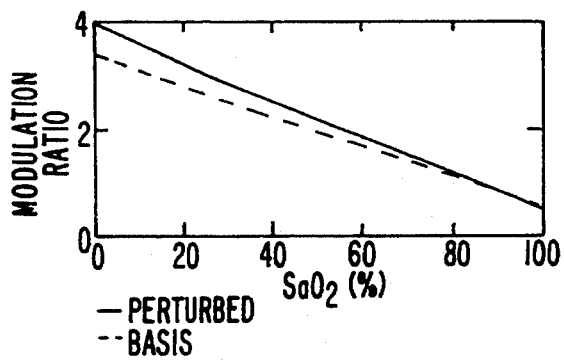
FIGS. 7(a)-7(b) –18(a)–18(b) are graphs showing experimental modeling of the modulation ratio and saturation error as a function of saturation for different red and infrared wavelength combinations.
Figure 7B:
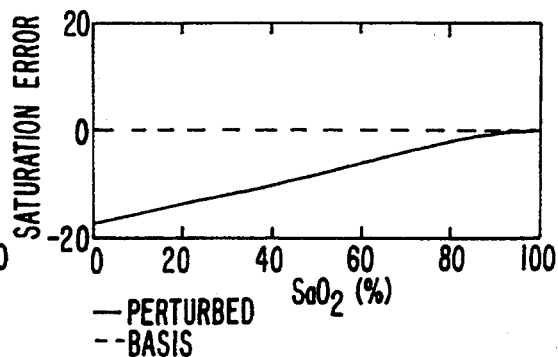
Figure 8A:
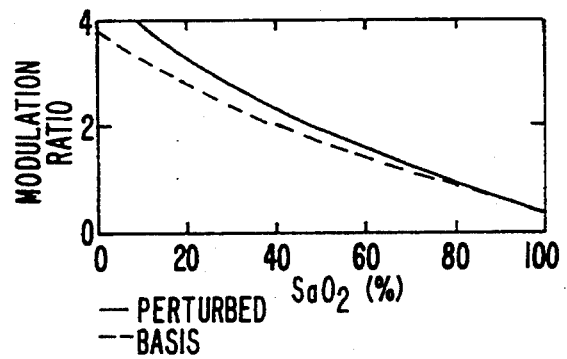
Figure 8B:
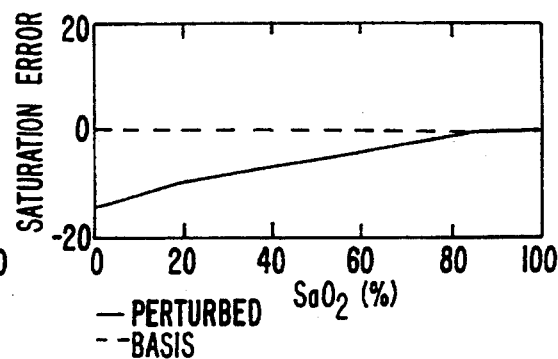
Figure 9A:
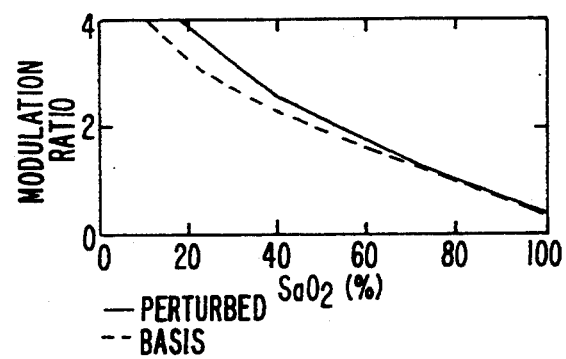
Figure 9B:
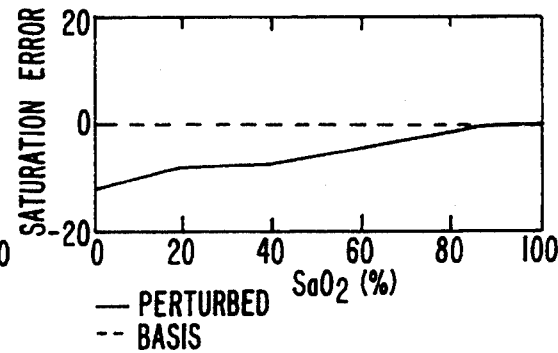
Figure 10A:
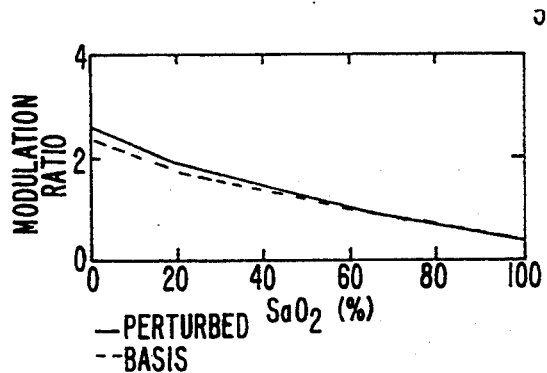
Figure 10B:
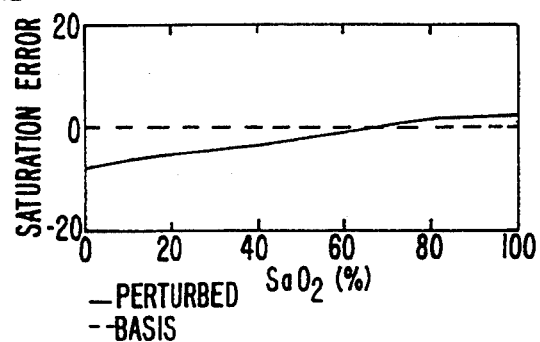
Figure 11A:
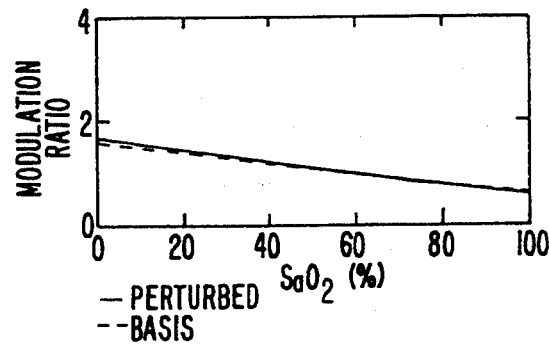
Figure 11B:
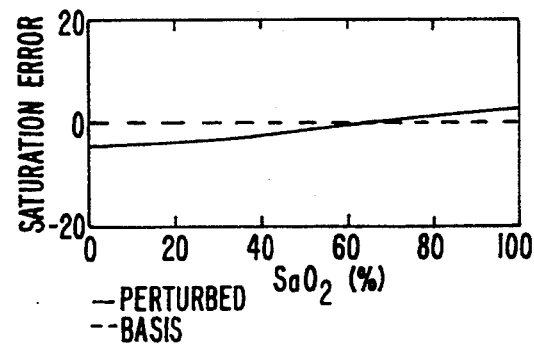
Figure 12A:
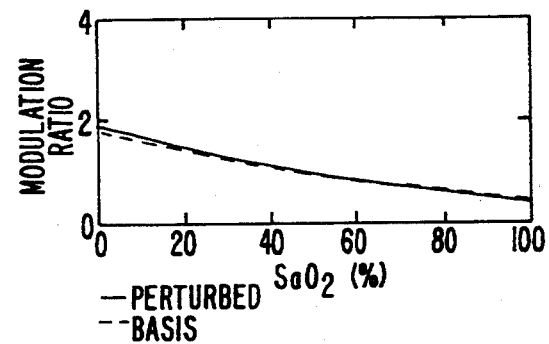
Figure 12B:
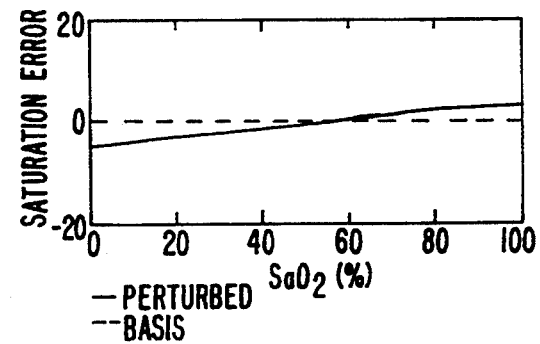
Figure 13A:
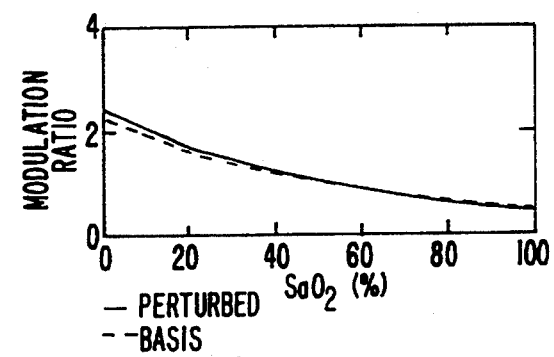
Figure 13B:
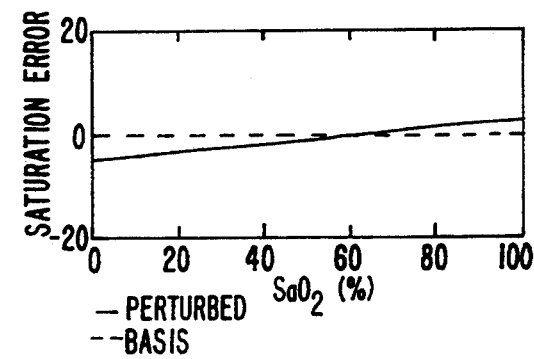
Figure 14A:
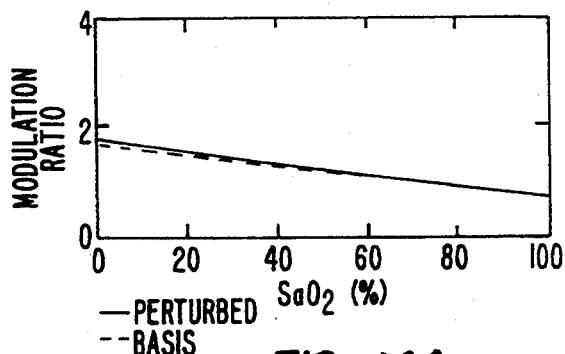
Figure 14B:
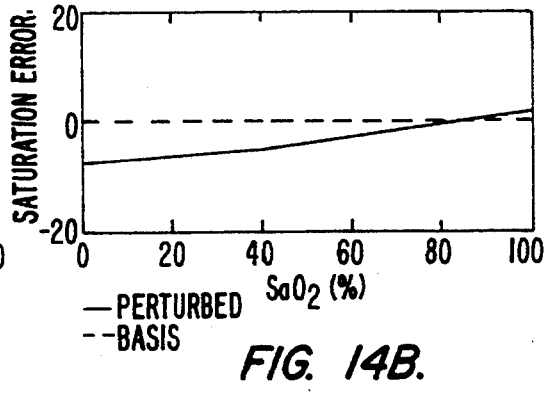
Figure 15A:
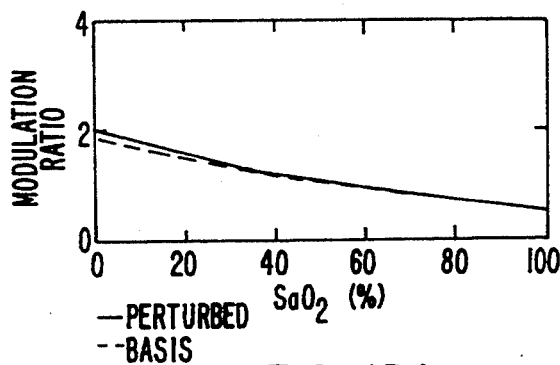
Figure 15B:
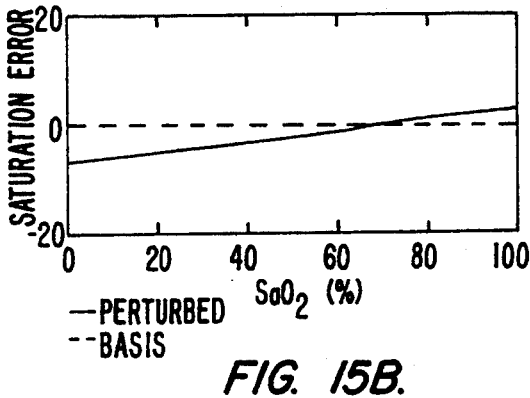
Figure 16A:
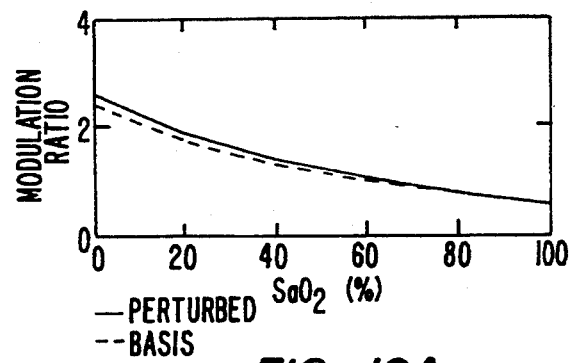
Figure 16B:
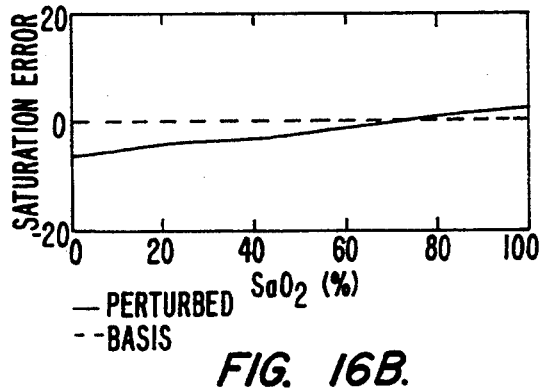
Figure 17A:
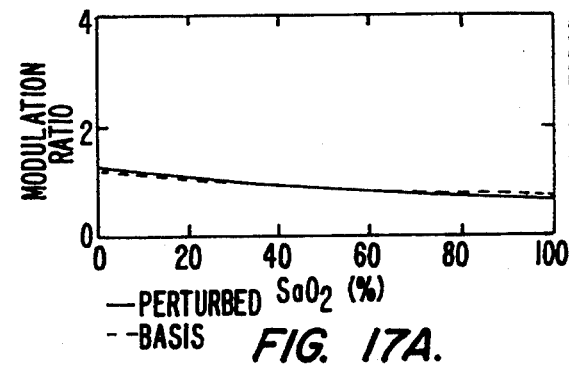
Figure 17B:
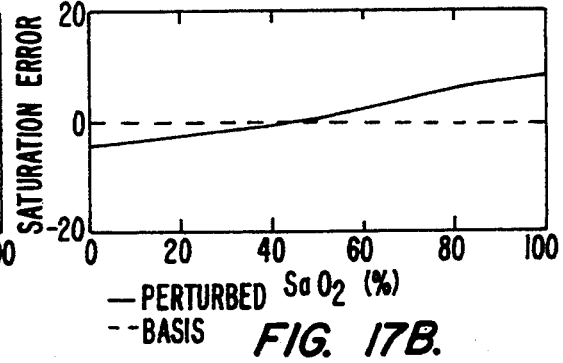
Figure 18A:
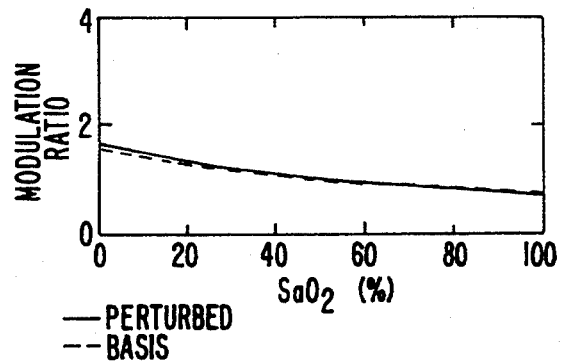
Figure 18B:
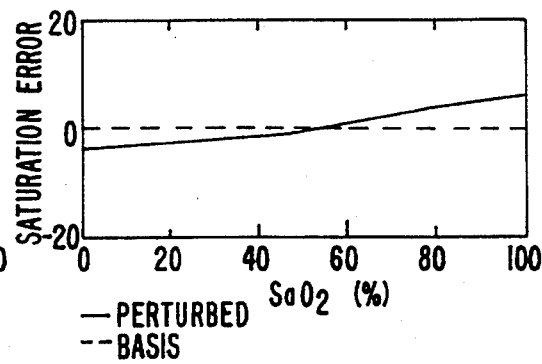

FIGS. 7-9 show the type of performance found in conventional pulse oximeters. FIGS. 10-18 show shifting of the optimum performance region from saturations above 80% to lower saturations when the "red" LED wavelength is chosen in the 700 nm-790 nm region of the spectrum. Light scattering is minimally affected by changes in oxygenation, but light absorption is significantly affected as reduced hemoglobin in the tissue changes to oxyhemoglobin or vice-versa. Pulse oximetry's optimum performance region occurs when there is a balance of the two channels' scattering and absorption properties within blood perfused tissue. Balance occurs when there is a good overlap of the volumes of tissue probed by the two channels, requiring that the penetration depth of light at the two wavelengths be matched. At the higher saturations, this optimum balance occurs with the pairing of wavelengths with a "red" emitter in the 660 nm band, while at the lower saturations the balance improves with the use of a "red" emitter in the 730 nm band. The variation of the IR LED from 805 to 940 nm does not produce a significant difference in performance.

Figure 1:
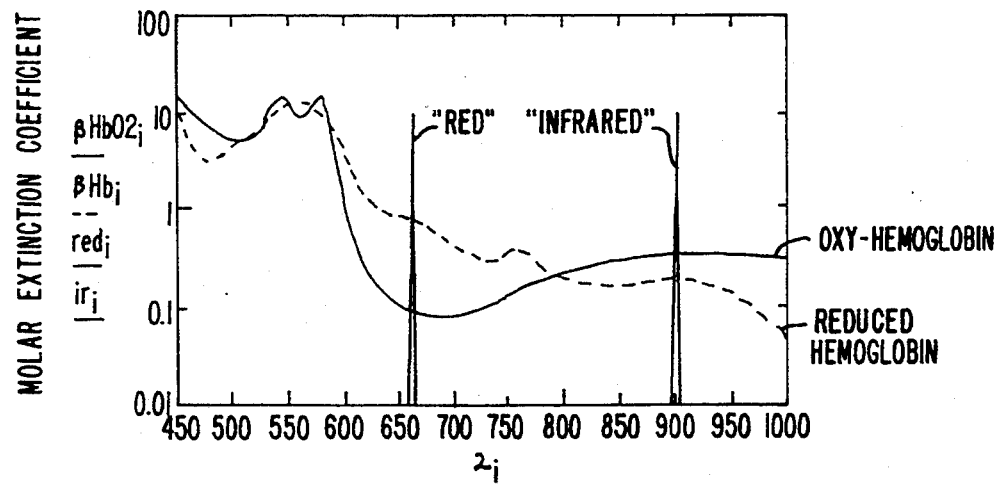
FIG. 1 is a chart of the absorption characteristics of oxyhemoglobin ($HbO_2$) and reduced hemoglobin (Hb) versus wavelength showing prior art red and infrared LED wavelengths.
Figure 2:
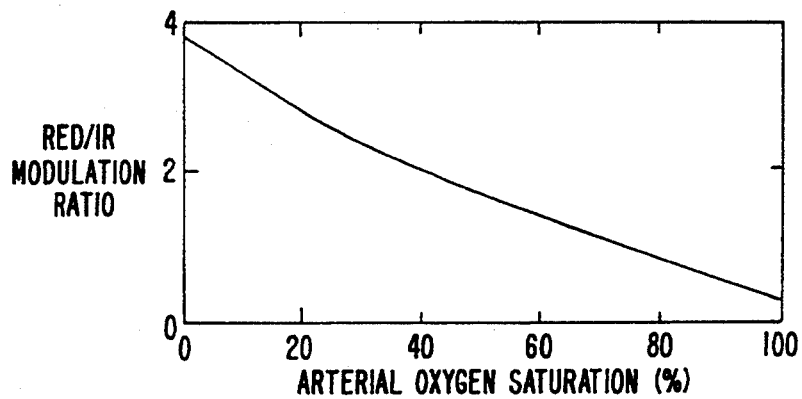
FIG. 2 is a graph of red/IR modulation ratio versus oxygen saturation.

When using an LED pair near 730 nm and 890 nm for pulse oximetry, the sensitivity of modulation ratio to changes in oxygen saturation (i.e., the slope of the curve in, for example, FIG. 1) is reduced relative to the use of 660 nm and 890 nm, but the measurement becomes more robust to changes in the tissue characteristics other than oxygen saturation. Noise in the measurement of modulation ratio due to factors such as instrument electronics noise, digitization, or ambient light interference, become more important but can generally be accounted for with good instrument design and appropriate signal processing. The bias and deviations due to tissue optical properties, however, become less significant with the proper choice of emitter wavelengths when they are chosen based on the saturation region of primary interest.

The inventors conducted empirical tests on sheep using prototype sensors. The empirical observations support the use of 735 nm band "red" LEDs in the design of a pulse oximeter that is more robust to perturbation induced artifacts at the lower saturation region. Reflectance pulse oximetry sensors were fabricated using conventional 660 nm-890 nm LED pairs, and with 735 nm-890 nm pairs.

FIGS. 19-23 show that measurements were taken at a range of oxygen saturation values indicated along the X axis from approximately 100% oxygen saturation to less than 10%. The plots show the calculated saturation ($SpO_2$) for each actual saturation ($SaO_2$) value. The actual saturation value is determined by simultaneously drawing blood samples from an arterial catheter placed in the left femoral artery. $SaO_2$ is measured on a laboratory co-oximeter (Instrument Labs IL 282 or Radiometer OSM-3). This is the value used on the X axis in these figures.

Figure 19:
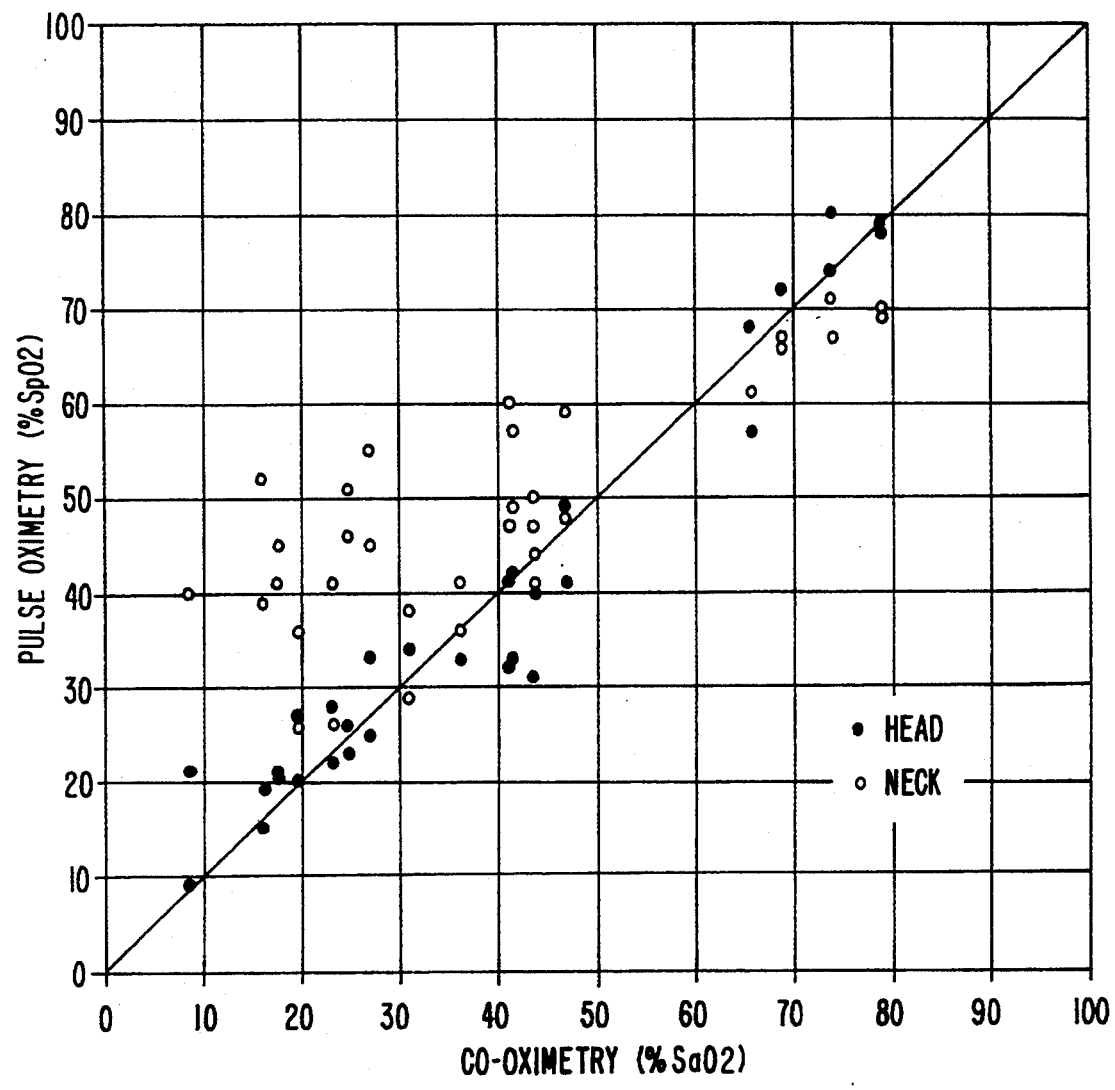
FIGS. 19–23 are charts illustrating saturation and the error due to applied force for different combinations of emitter wavelength and emitter-detector spacing from experiments done on sheep.
Figure 20:
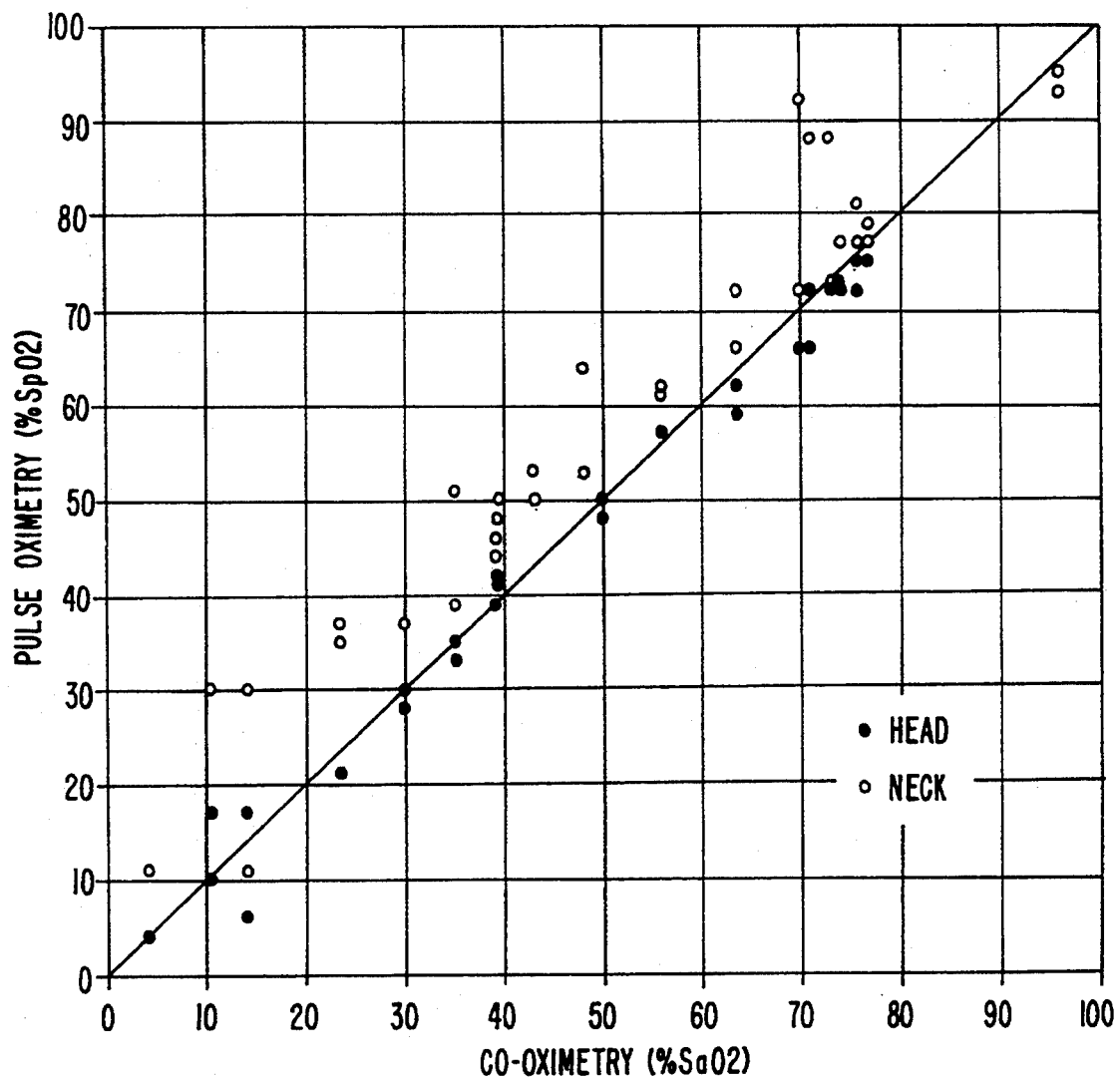
Figure 21:
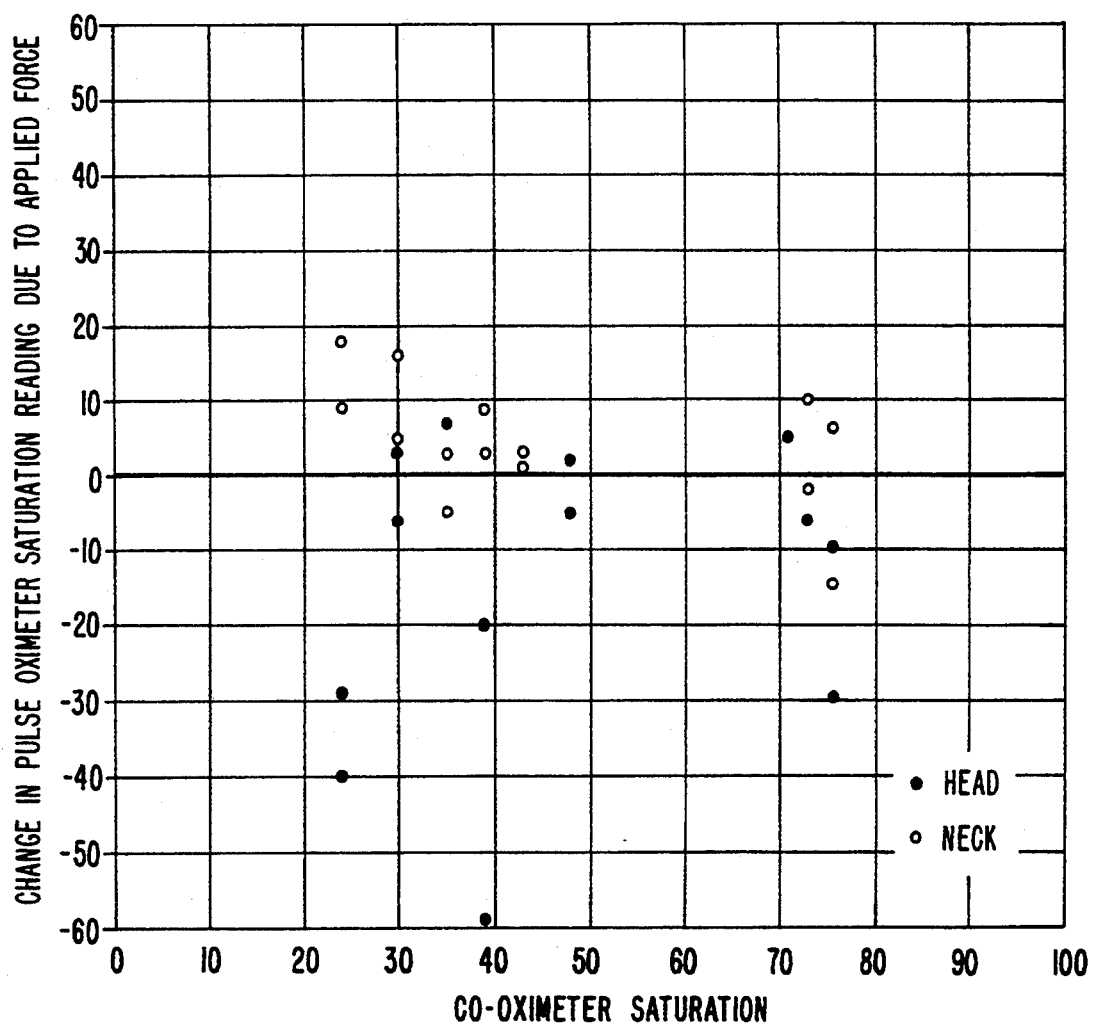
Figure 22:
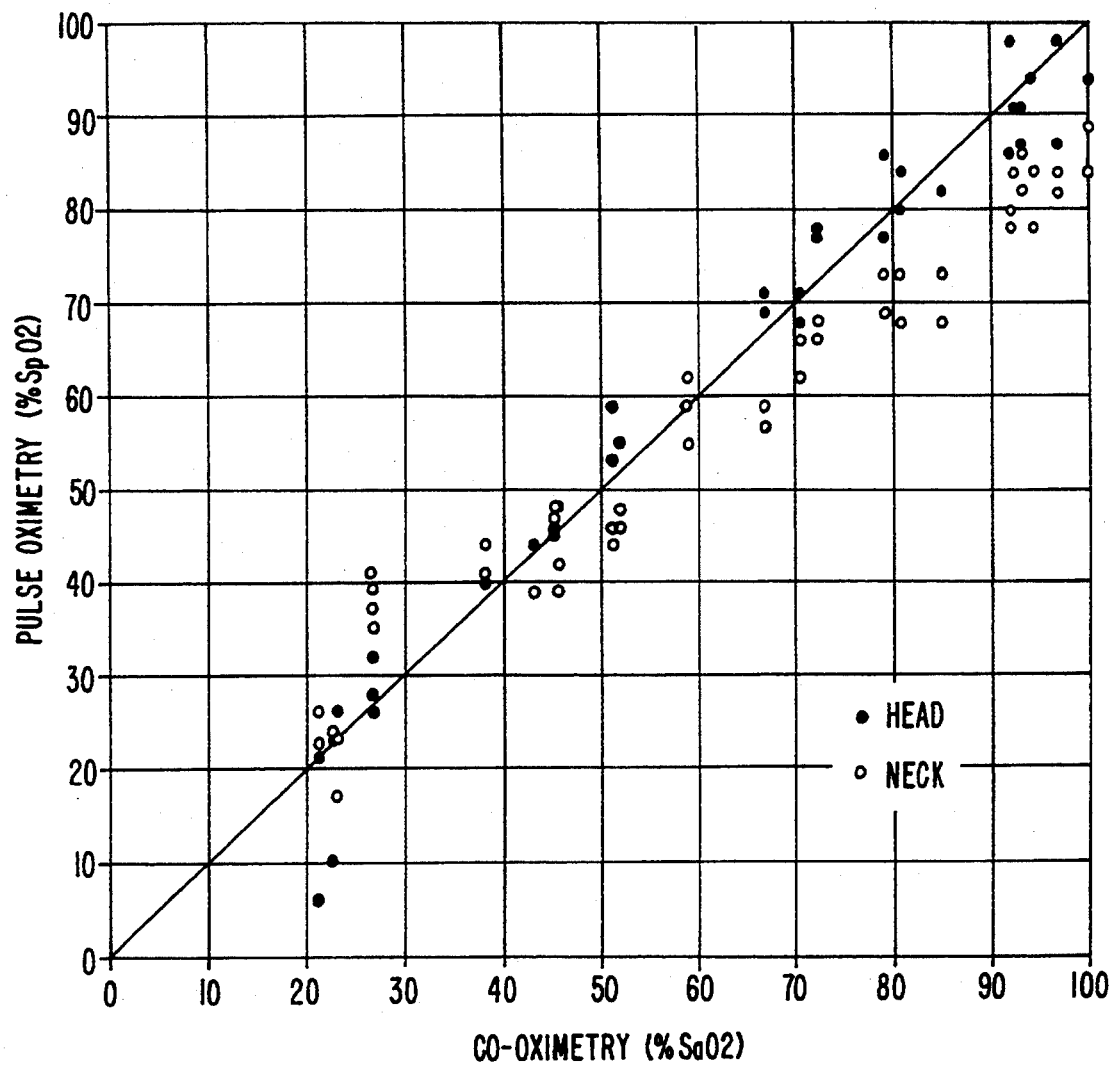

As can be seen, the diagonal line in FIGS. 19, 20, and 22 indicates the desired result where the calculated value is equal to the actual value as measured with the catheter. The tests illustrated in FIGS. 19, 20, and 22 were done with a nominal force of approximately 50 grams applied to the sensor holding it against the skin.

Using the 660 nm sensor with emitter/detection spacing of 14 mm, FIG. 19 shows that sensor calibration is very sensitive to the type of tissue probed. The calibration on the head and neck are very different.

Using the 735 nm sensor with a 5.8 mm emitter/detector spacing, the bias between the head and neck is greatly reduced as illustrated by FIG. 20. There is, however, still substantial sensitivity to surface exsanguination. This is apparent in FIG. 21 which illustrates the effect of a perturbation induced artifact (sensor applied force).

Figure 23:
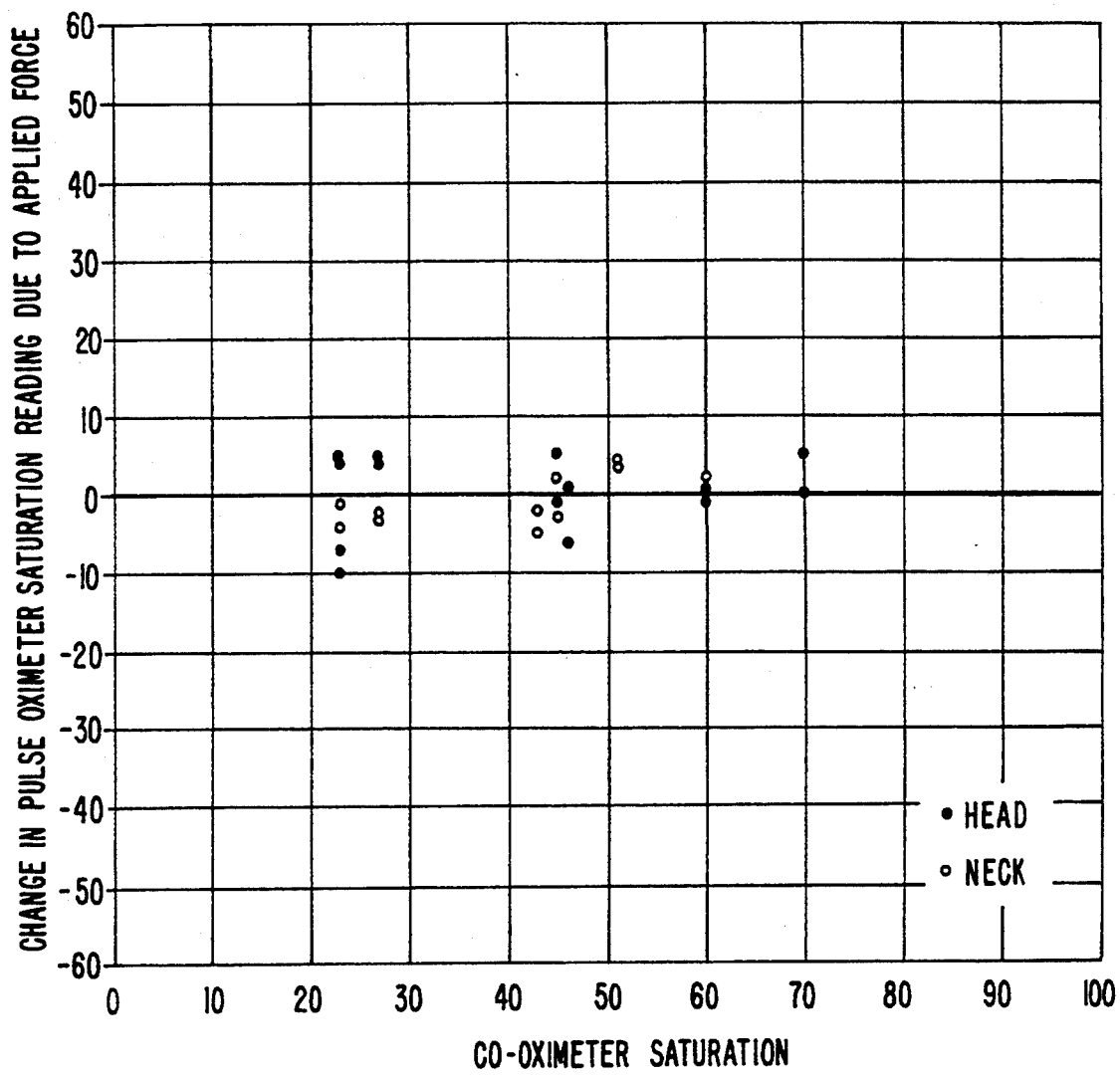

FIG. 22 shows the location insensitivity of a 735 nm sensor with a 14 mm emitter/detector spacing. FIG. 23 shows that this sensor is also insensitive to force applied to the sensor (perturbation induced artifact).

It was experimentally confirmed that increasing the emitter/detector spacing from 5.8 mm for 735 nm/890 nm LED wavelengths decreased the sensitivity to perturbation induced artifacts, with good performance being achieved by an emitter/detector separation equal to or greater than 10 mm.

Both the modeling and the actual experiments illustrate an improvement in reliability of a saturation measurement achieved by optimizing the red wavelength to be within 700-790 nm range. In addition, reduction of the saturation error reading in the presence of force artifact is achieved by increasing the spacing of the emitters from the detector.

The force applied to the sensor causes exsanguination of the surface tissue, further magnifying the remaining disparities due to the inhomogeneity of the tissue, or causing shunting of light between the emitter and detector, thus causing errors in the saturation calculation. These are compensated for by wider emitter/detector spacing, which results in the light from the red and infrared LEDs penetrating deeper into the tissue, thus increasing the likelihood of their going through, on the average, the same combination of tissue structures, as illustrated in FIG. 3.

Figure 24:
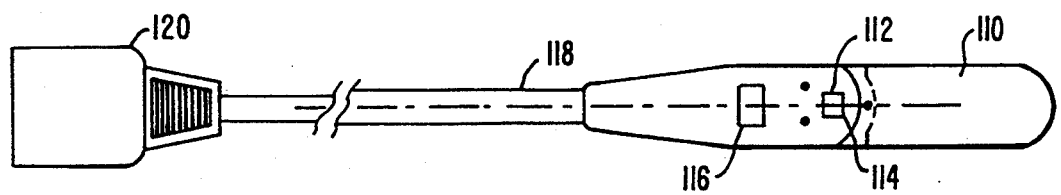
FIGS. 24 and 25 are diagrams illustrating the construction of a sensor according to the present invention.
Figure 25:
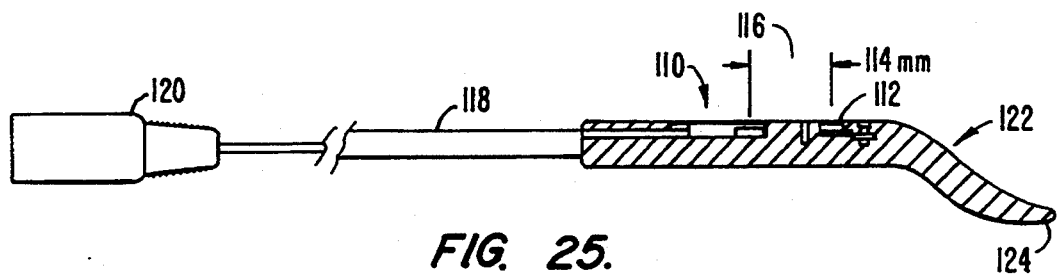

FIG. 24 is a top view of a sensor according to one embodiment of the present invention. The sensor face 110 supports a red LED 112 and an infrared LED 114. These are spaced by 14 mm from a detector 116. Preferably, the centers of the red and infrared LEDs are no more than 0.5 mm apart. The sensor face is connected by a cable 118 to a connector 120 for connection to the pulse oximeter monitor. FIG. 25 shows a side view of the sensor of FIG. 24, illustrating the fulcrum portion 122 of the sensor and sensor back 132. When placed in utero, the uterus will apply a force to the sensor back 132 and deform the fulcrum 122. As can be seen, this technique results in a force being applied to the sensor resulting in good sensor-fetus contact but possibly resulting in exsanguination of the tissue.

The modeling and empirical tests show that the nature of the correlation between modulation ratio and saturation in pulse oximetry is related to tissue optical properties, and that the sensitivity to varying perturbation induced artifacts can be affected by choice of emitter wavelengths. For high oxygen saturations, the choice of 660 nm and 890 nm band emitters is well suited for stable pulse oximetry calculations, while 700–790 nm and 890 nm band emitters perform better at low saturations. Other wavelength combinations may be chosen from elsewhere in the visible and near infrared portion of the spectrum by following an analysis similar to the one described here. Currently, however, overall instrument design considerations (e.g., electronic signal-to-noise and potential shunting of light with narrowly spaced components in a reflectance probe) favor the use of the wavelengths discussed. By using the analysis described, other improvements to pulse oximetry are possible. FIGS. 19–23 illustrate the results of these tests for several prototype sensors.

As will be understood by those with skill in the art, the present invention can be embodied in other specific forms without departing from the essential characteristics thereof. For example, a pulse oximeter for use over a broad saturation range can utilize multiple wavelength pairs (e.g., both 660 nm and 730 nm band emitters coupled with a 900 nm emitter), with the appropriate emitter pair chosen for use in the calculation of $SpO_2$ based on the estimated value of the oxygen saturation. Lasers or other light sources could be used rather than LEDs, or the wavelength could be varied while still optimizing in accordance with the present invention. Different sensors than the fulcrum structure as set forth in FIG. 25 could be used, such as a bladder structure for inflating and holding the sensor against the fetus. Accordingly, reference should be made to the appended claims for defining the scope of the invention.

What is claimed is:

1. A method for using a pulse oximeter to measure blood oxygen saturation, comprising the steps of:
   providing a sensor and a pulse oximeter;
   selecting a light source for said sensor;
   optimizing a wavelength spectrum of said light source for an oxygen saturation reading less than 80 percent;
   placing said sensor on a patient; and
   determining said blood oxygen saturation using said sensor and said pulse oximeter.

2. The method of claim 1, wherein said optimizing step is for an oxygen saturation of a fetus.

3. The method of claim 2 including optimizing said wavelength spectrum wherein the for an oxygen saturation reading less than 65 percent.

4. The method of claim 2 including optimizing said wavelength spectrum for an oxygen saturation reading greater than 15%.

5. The method of claim 4 wherein said spacing of said light source from said detector is at least 10 mm.

6. The method of claim 2 further comprising the step of:
   placing a detector on said sensor;
   optimizing a spacing of said light source from said detector to reduce the sensitivity of said sensor to perturbation induced artifact; and
   measuring the intensity of light from said light source at said detector using reflectance of the light through said fetus.

7. The method of claim 2 wherein said light source comprises a red and an infrared light source, said optimizing step comprising using an infrared light source in a range useful for adults, and optimizing the wavelength spectrum of said red light source for a fetus.

8. The method of claim 7 wherein the mean wavelength of said red light source is between 700 and 790 nanometers.

9. The method of claim 7 wherein the spectrum of said red light source includes 735 nanometers at an intensity of at least 50% of the intensity of any other wavelengths in said spectrum.

10. The method of claim 2 wherein said optimizing step increases a depth of penetration of said light in a fetus compared to optimum penetration depth for an adult.

11. The method of claim 1 wherein said light source comprises a red and an infrared light source, each of said red and infrared light source having an extinction and a scattering coefficient for blood perfused tissue, said optimizing step comprising choosing wavelengths of said red and infrared light source whose product of their extinction and scattering coefficients form first and second values, a ratio between said first and second values being between 0.5 and 2 for a majority of the oxygen saturation reading range of 0 to 65 percent.

12. The method of claim 1 wherein said optimizing step reduces the sensitivity of said determining step to artifact and decreases the sensitivity to changes in saturation.

13. A method for using a pulse oximeter to measure blood oxygen saturation in a fetus, comprising the steps of providing a sensor and a pulse oximeter;
   selecting a red and an infrared light source for said sensor, said infrared light source having a wavelength spectrum useful for measuring oxygen saturation in an adult;
   optimizing a wavelength spectrum of said red light source to a mean wavelength between 700 and 790 nanometers for an oxygen saturation reading between 15 and 65 percent, said optimizing increasing the immunity of a measurement of blood oxygen saturation to exsanguination artifact due to pressure of said sensor against said fetus;
   placing said sensor on said fetus;
   measuring an intensity of light from said light sources at a detector after reflectance through a portion of said fetus; and
   determining said blood oxygen saturation using said intensity and said pulse oximeter.

14. A method for using a pulse oximeter to measure blood oxygen saturation in a fetus, comprising the steps of providing a sensor and a pulse oximeter;
   selecting red and an infrared light source, each of said red and infrared light source having an extinction and a scattering coefficient for blood perfused tissue,;
   optimizing a wavelength spectrum of said light sources by choosing wavelengths of said red and infrared light source whose product of their extinction and scattering coefficients form first and second values, a ratio between said first and second values being between 0.5 and 2 for a majority of the oxygen saturation reading range of 0 to 65 percent;

placing said sensor on said fetus; and determining said blood oxygen saturation using said sensor and said pulse oximeter.

* * * * *